United States Patent
Aljuri et al.

(10) Patent No.: US 7,882,841 B2
(45) Date of Patent: Feb. 8, 2011

(54) MINIMALLY INVASIVE METHODS AND DEVICES FOR THE TREATMENT OF PROSTATE DISEASES

(75) Inventors: Nikolai Aljuri, San Francisco, CA (US); Rodney C. Perkins, Woodside, CA (US)

(73) Assignee: Procept Corporation, Woodside, CA (US)

( * ) Notice: Subject to any disclaimer, the term of this patent is extended or adjusted under 35 U.S.C. 154(b) by 30 days.

(21) Appl. No.: 11/968,445

(22) Filed: Jan. 2, 2008

(65) Prior Publication Data

US 2009/0018533 A1    Jan. 15, 2009

Related U.S. Application Data

(60) Provisional application No. 60/883,097, filed on Jan. 2, 2007.

(51) Int. Cl.
*A61B 19/00* (2006.01)
(52) U.S. Cl. .................. 128/898; 607/143; 606/171
(58) Field of Classification Search .................. 606/47, 606/34, 170, 21, 2–19, 167, 171; 607/33–34, 607/39, 41, 45, 50, 101, 103–105, 143; 128/898
See application file for complete search history.

(56) References Cited

U.S. PATENT DOCUMENTS

| | | |
|---|---|---|
| 3,847,988 A | 11/1974 | Gold |
| 3,875,229 A | 4/1975 | Gold |
| 4,097,578 A | 6/1978 | Perronnet et al. |
| 4,220,735 A | 9/1980 | Dieck et al. |
| 4,239,776 A | 12/1980 | Glen et al. |
| 4,377,584 A | 3/1983 | Rasmusson et al. |
| 4,386,080 A | 5/1983 | Crossley et al. |
| 4,461,283 A | 7/1984 | Doi |
| 4,636,505 A | 1/1987 | Tucker |
| 4,760,071 A | 7/1988 | Rasmusson et al. |
| 5,116,615 A | 5/1992 | Gokcen et al. |
| 5,322,503 A | 6/1994 | Desai |
| 5,454,782 A * | 10/1995 | Perkins ................... 604/20 |
| 5,496,267 A * | 3/1996 | Drasler et al. ............ 604/22 |
| 5,562,703 A | 10/1996 | Desai |
| 5,630,794 A | 5/1997 | Lax et al. |

(Continued)

FOREIGN PATENT DOCUMENTS

WO    WO 92/10142    6/1992

(Continued)

OTHER PUBLICATIONS

Boffo et al., "Electrovaporization of the Prostate with the Gyrus Device," *J. Endourol.* (Apr. 2001) 15(3):313-316.

(Continued)

*Primary Examiner*—Ahmed M Farah
(74) *Attorney, Agent, or Firm*—Townsend and Townsend and Crew LLP

(57) ABSTRACT

Methods and systems for resecting and debulking prostatic tissue to utilize a shaft carrying an energy source. The shaft is anchored by a balloon or other structure expanded in the bladder, and the energy source is capable of directing ablative energy radially outwardly from the urethra, where the energy source will be moved in order to remove a pre-defined volume of prostatic tissue.

12 Claims, 7 Drawing Sheets

U.S. PATENT DOCUMENTS

| | | | |
|---|---|---|---|
| 5,672,153 A * | 9/1997 | Lax et al. ................. 604/22 |
| 5,672,171 A | 9/1997 | Andrus et al. |
| 5,753,641 A | 5/1998 | Gormley et al. |
| 5,770,603 A | 6/1998 | Gibson |
| 5,817,649 A | 10/1998 | Labrie |
| 5,861,002 A | 1/1999 | Desai |
| 5,872,150 A | 2/1999 | Elbrecht et al. |
| 5,994,362 A | 11/1999 | Gormley et al. |
| 6,022,860 A | 2/2000 | Engel et al. |
| 6,142,991 A | 11/2000 | Schatzberger |
| 6,179,831 B1 | 1/2001 | Bliweis |
| 6,200,573 B1 | 3/2001 | Locke |
| 6,217,860 B1 | 4/2001 | Woo et al. |
| 6,231,591 B1 | 5/2001 | Desai |
| 6,296,639 B1 | 10/2001 | Truckai et al. |
| 6,378,525 B1 | 4/2002 | Beyar et al. |
| 6,413,256 B1 | 7/2002 | Truckai et al. |
| 6,425,877 B1 * | 7/2002 | Edwards ................. 604/21 |
| 6,814,731 B2 * | 11/2004 | Swanson ................. 606/32 |
| 6,821,275 B2 | 11/2004 | Truckai et al. |
| 6,890,332 B2 | 5/2005 | Truckai et al. |
| 7,015,253 B2 | 3/2006 | Escandon et al. |
| 2001/0048942 A1 | 12/2001 | Weisman et al. |
| 2002/0010502 A1 * | 1/2002 | Trachtenberg ............ 607/102 |
| 2002/0040220 A1 | 4/2002 | Zvuloni et al. |
| 2002/0111617 A1 * | 8/2002 | Cosman et al. ............ 606/41 |
| 2003/0060819 A1 | 3/2003 | McGovern et al. |
| 2003/0065321 A1 * | 4/2003 | Carmel et al. ............ 606/41 |
| 2005/0010205 A1 * | 1/2005 | Hovda et al. ............ 606/41 |
| 2005/0054994 A1 | 3/2005 | Cioanta et al. |
| 2005/0165383 A1 * | 7/2005 | Eshel et al. ............ 604/544 |
| 2005/0288639 A1 | 12/2005 | Hibner |
| 2005/0288665 A1 | 12/2005 | Woloszko |
| 2006/0129125 A1 | 6/2006 | Copa et al. |
| 2006/0167416 A1 * | 7/2006 | Mathis et al. .......... 604/164.01 |
| 2006/0178670 A1 * | 8/2006 | Woloszko et al. .......... 606/48 |
| 2008/0154258 A1 * | 6/2008 | Chang et al. ............ 606/41 |
| 2010/0145254 A1 * | 6/2010 | Shadduck et al. .......... 604/20 |

FOREIGN PATENT DOCUMENTS

WO      WO 93/15664      8/1993

OTHER PUBLICATIONS

Stalder et al., "Repetitive Plasma Discharges in Saline Solutions," *Appl. Phys. Lett.* (Dec. 2001), 79(27):4503-4505.

Woloszko et al., "Plasma Characteristics of Repetitively-Pulsed Electrical Discharges in Saline Solutions Used for Surgical Procedures," (2002) *IEEE Trans. Plasma Sci.* 30(3):1376-1383.

Yang et al. "The Development of the Water Jet Scalpel With Air Pressure," *Trans. ASME* (Jun. 2001), 123(2):246-248.

International Search Report and Written Opinion of PCT Application No. PCT/US08/50051, dated May 20, 2008, 10 pages total.

* cited by examiner

MINIMALLY INVASIVE METHODS AND DEVICES FOR THE TREATMENT OF PROSTATE DISEASES

CROSS REFERENCE TO RELATED APPLICATIONS

This application claims the benefit of provisional application 60/883,097, filed on Jan. 2, 2007, the full disclosure of which is incorporated herein by reference.

BACKGROUND OF THE INVENTION

1. Field of the Invention

The present invention relates generally to medical methods and devices. In particular, the present invention relates to methods and devices for applying energy to the urethra to achieve volumetric tissue reduction.

A number of medical conditions affect the male urethra causing a variety of symptoms including painful or difficult urination, a swollen prostate, blood in the urine, lower back pain, and the like. Some of these conditions, such as prostatitis, are bacterial infections which can be treated with antibiotics and other drugs. Other conditions, however, such as benign prostatic hyperplasia (BPH) and prostatic carcinoma, result in enlargement of the prostate and obstruction of the urethra, sometimes leading to complete loss of bladder function.

Both BPH and prostatic cancer require treatments which remove or shrink tissue in the prostate surrounding the urethra. Common treatments include transurethral resection of the prostate (TURP) where a resectoscope is placed in the urethra and used to remove excess prostatic tissue. Another procedure, referred to as transurethral incision of the prostate (TUIP), relies on cutting muscle adjacent to the prostate to relax the bladder opening to relieve difficulty in urination. More recently, a procedure referred to as transurethral needle ablation (TUNA) has been introduced where a needle is advanced through the urethra into the prostate and used to deliver energy, such as microwave, radiofrequency, or ultrasound energy, to reduce the size of the prostate, again relieving pressure on the urethra. Laser ablation using transurethral optical fibers also finds use.

While generally successful, none of these methods are adequate to treat all patients and all conditions. In particular, patients having severe tissue intrusion into the urethral lumen resulting from BPH or prostatic cancer are difficult to treat with minimally invasive protocols which rely on tissue shrinkage rather than resection. Thus, many of these patients will eventually require conventional surgical resection.

For these reasons, it would be desirable to provide minimally invasive methods and devices which provide for enlarging the luminal area and/or volumetric resection of tissue surrounding the urethra. It would be particularly desirable if such methods and devices provided for removal or destruction of such tissues surrounding the urethra where the removal or destruction products can be removed from the lumen to relieve pressure on the urethra, even where large volumes of tissue have been removed. Alternatively or additionally, the methods and devices should provide for anchoring of the treatment device relative to the urethra in order to provide a stable platform for treatment protocols which do not require visualization. Methods and devices for performing such protocols should present minimal risk to the patient, should be relatively easy to perform by the treating physician, and should allow for alleviation of symptoms with minimal complications even in patients with severe disease. At least some of these objectives will be met by the inventions described below.

2. Description of the Background Art

Use of a transurethral endoscope for bipolar radiofrequency prostate vaporization is described in Boffo et al. (2001) *J. Endourol.* 15:313-316. Radiofrequency discharge in saline solutions to produce tissue-ablative plasmas is discussed in Woloszko et al. (2002) *IEEE Trans. Plasma Sci.* 30:1376-1383 and Stalder et al. (2001) *Appl. Phys. Lett.* 79:4503-4505. Air/water jets for resecting tissue are described in Jian and Jiajun (2001) *Trans. ASME* 246-248. US2005/0288639 described a needle injector on a catheter based system which can be anchored in a urethra by a balloon in the bladder. U.S. Pat. Nos. 6,890,332; 6,821,275; and 6,413,256 each describe catheters for producing an RF plasma for tissue ablation. Other patents and published applications of interest include: U.S. Pat. Nos. 7,015,253; 6,890,332; 6,821,275; 6,413,256; 6,378,525; 6,296,639; 6,231,591; 6,217,860; 6,200,573; 6,179,831; 6,142,991; 6,022,860; 5,994,362; 5,872,150; 5,861,002; 5,817,649; 5,770,603; 5,753,641; 5,672,171; 5,630,794; 5,562,703; 5,322,503; 5,116,615; 4,760,071; 4,636,505; 4,461,283; 4,386,080; 4,377,584; 4,239,776; 4,220,735; 4,097,578; 3,875,229; 3,847,988; US2002/0040220; US2001/0048942; WO 93/15664; and WO 92/10142.

BRIEF SUMMARY OF THE INVENTION

Methods, devices, and systems according to the present invention provide for intraluminal delivery of energy, to ablate or resect tissue surrounding a urethra. The present invention is particularly intended for treating benign prostatic hyperplasia (BPH) and prostatic carcinoma, both of which can result in compression and partial or total occlusion of the urethra. Treatments comprise positioning an energy source within the urethra and directing energy radially outwardly from the energy source toward the urethral wall within the prostate. The energy source will usually be moved relative to the urethra to remove a pre-defined volume of prostate tissue surrounding the urethral lumen in order to partially or fully relieve the compression and/or obstruction. In other embodiments, however, the therapy may comprise mechanical, thermal, acoustic or vibrational, cryotherapy or other forms of treatment for BPH and other conditions. Optionally, the treatments of the present invention may be combined with chemotherapy and other forms of drug delivery, as well as treatment with external X-ray and other radiation sources and administration of radiopharmaceuticals comprising therapeutic radioisotopes. For example, one or more drugs may be combined with the saline or other fluid which is used for energy delivery. The combination liquid/gas delivery can be used to both resect tissue and wash the tissue away while leaving intra-prostatic blood vessels, capsule, and sphincter muscle undamaged. Thus, benefits of the high pressure liquid/gas energy source include limited bleeding with reduced or no need for cauterization and decreased risk of perforating or otherwise damaging the capsule of sphincter muscles. Alternatively, the device which is used to position the energy source can be utilized to separately deliver a desired chemotherapeutic or other drug (as just set forth), either before, during, or after energy treatment according to the present invention. While the present invention is specifically directed at transurethral treatment of the prostate, certain aspects of the invention may also find use in the treatment of other body lumens, organs, passages, tissues, and the like, such as the ureter, colon, esophagus, lung passages, bone marrow, and blood vessels.

Thus, in a first aspect of the present invention, methods for resecting and removing prostate tissue comprise positioning an energy source within the urethra and directing energy radially outwardly from the energy source toward a wall of the urethra within the prostate. The energy source is then moved relative to the urethra to remove a pre-defined volume of tissue surrounding the lumen. In a particular aspect of the present invention, the method further comprises expanding an anchor within the bladder at the distal end of the urethra. The energy source is then positioned and moved relative to the anchor to assure that the treatment is properly directed to prostatic tissue. The use of the anchor is particularly advantageous since it allows the procedures to be performed without endoscopic, fluoroscopic, or other imaging. The methods of the present invention, of course, do not exclude such imaging, but rather permit the methods to be performed when desired without further imaging.

Usually, the energy source and the anchor will be mounted on a common catheter assembly, more typically on a single shaft. Thus, the catheter assembly or shaft may be maintained in a fixed or immobilized position within the urethra by either applying a tension which engages the anchor against the bladder wall, or preferably by expanding the anchor fully within the bladder to reduce the risk that the catheter assembly or shaft can be accidentally dislodged.

The energy source can be any one or a combination of various conventional energy sources which can be used to resect or ablate tissues. A first exemplary energy source comprises high pressure fluids, such as water, saline, liquid therapeutic agent, or the like. The high pressure fluid is often a combination of a liquid and gas, such as water and air, and can be delivered radially outwardly in one or more fluid streams which impinge directly against the urethral wall and prostatic tissue to resect or debulk the tissue. The fluid stream(s) may be directed at a generally perpendicular or normal angle relative to a catheter assembly or shaft, and may also be directed at other angle(s), typically in the range from 10° to 90°, more typically from 45° to 90°, relative to the shaft or catheter assembly which carries the port or ejector used to deliver the fluid(s) including, for example, anesthetics, antibiotics, anti-inflammatories, anti-neoplastics, tissue-specific growth factors, anti-growth factors, hormones, anti-hormones, vasodilators, vitamins, proteins, and the like.

The energy source may also deliver laser energy used to ablate tissue. The laser energy will usually be delivered by an optical waveguide or fiber bundle carried within a catheter assembly or shaft which is introduced through the urethra. The laser energy can then be directed radially outwardly either by deflecting the shaft and/or by using a mirror to reflect the energy. The mirror may optionally have a surface which focuses or defocuses the energy in a desired manner as it is delivered to the prostatic tissue.

A third suitable energy source comprises an electrically conductive fluid which carries radiofrequency current, optionally generating a plasma of the conductive fluid. One or more streams of such electrically conductive fluids may be directed outwardly through ceramic nozzles or other distribution elements.

A fourth energy source comprises an electrode adapted to deliver radiofrequency energy. The electrode will have a deflected or deflectable distal end which can be directed radially outwardly from a catheter assembly or shaft which carries the electrode into the urethra. The tip or other surface of the electrode can thus be engaged against the urethral wall and prostatic tissue in order to deliver ablative radiofrequency energy into the tissue.

The methods of the present invention may further comprise associated steps and processes to assist in the tissue resection and ablation. In order to gain a working space within the urethra, the methods may further comprise introducing a pressurized gas to expand (insufflate) the urethra lumen prior to or while directing the energy radially outwardly into the prostatic tissue. Further optionally, the ablation or resection products may be aspirated from the urethra, typically through a lumen in the catheter assembly or shaft used to deliver the energy source. In combination with aspiration, the urethra may also be flushed with saline or other fluid to assist in removing the ablation or resection products. Usually, both flushing and aspiration will be performed using lumens in the same catheter assembly or shaft which has been used to position the energy source.

The energy source will be moved in a pre-defined manner relative to the anchored shaft or urethra in order to selectively treat the prostatic tissue. Typically, the energy source will be moved to cover and treat a cylindrical volume of prostatic tissue surrounding the urethra. In such cases, the energy source will typically be rotated and/or axially translated within the urethra so that the energy is uniformly delivered into the urethral wall. Alternatively, the energy source may be scanned to a non-cylindrical and optionally non-symmetric region within the urethra which has been targeted for treatment. Various combinations of rotation, axial translation, rotational oscillation, and axial oscillation may be used.

In a separate aspect of the present invention, methods for treating a prostate comprise advancing a shaft through a urethra. An anchor on the shaft is expanded in a bladder to stabilize the shaft in the urethra, that is to fix the position relative to the urethral wall. The treatment device on the shaft is then activated to enlarge the urethra and/or debulk the prostate, where the position of the treatment device is fixed by the anchor. Usually, the anchor comprises a balloon which is inflated within the bladder, typically being inflated to fully occupy the entire volume of the urethra so that the risk of dislodgement is reduced. Actuating the treatment device may comprise use of any one of the energy sources described above, broadly including applying mechanical, vibrational, thermal, optical, and/or electrical energy to the prostatic tissue from the stabilized shaft. Usually, the treatment device will be moved relative to the shaft to treat a pre-defined surface region of the urethra, where the pre-defined surface region is usually cylindrical but may be non-cylindrical and non-symmetric as also described above. Typically, the treatment device emits a stream or circumferential band of energy, where movement comprises at least axial translation and/or axial oscillation. Usually, movement will further comprise rotation and/or rotational oscillation.

In addition to the methods described above, the present invention also provides prostate resection devices comprising a shaft, an expandable anchor, and at least one energy source. The shaft has a proximal end and a distal end. The expandable anchor is positioned on the shaft near its distal end and is adapted for anchoring within the bladder. The at least one energy source is also on the shaft and is spaced proximally of the anchor by a distance selected to position the energy source within a desired region of the urethra, typically within the prostate, when the anchor is positioned in the bladder. Thus, the energy may be delivered radially outwardly from the energy source selectively into the target prostate tissue without the need for imaging or other positioning methods or apparatus.

The prostate resection devices of the present invention may further comprise various lumens in the shaft for performing supplemental portions of the procedure. For example, the shaft may comprise one or more lumens for delivering a gas or fluid to pressurize and enlarge (insufflate) the urethra surrounding the energy source. One or more additional lumens may be provided for aspirating the urethra to remove ablation products and/or for delivering fluids to flush the urethra to remove ablation or resection products. The shaft will be adapted for delivery in a retrograde direction into the male urethra, typically having a width in the range from 1 mm to 10 mm and a length in the range from 15 cm to 25 cm.

The prostate resection devices of the present invention may comprise any of the various energy sources described above. Usually, the energy source will be movable relative to the shaft to allow for selectively directing energy at different regions of the prostate. More typically, the energy source may be translated, rotated, translationally oscillated, and/or rotationally oscillated relative to the shaft. Exemplary energy sources comprise a high pressure fluid ejector, such as a nozzle or other port connected to additional lumen(s) in the shaft, a laser energy source, such as an optical fiber optionally combined with a mirror for reflecting the laser energy, a conductive fluid source in combination with a radiofrequency energy source, and/or an electrode that can be positioned against the urethral wall to deliver radiofrequency energy.

DETAILED DESCRIPTION OF THE INVENTION

Figure 1:
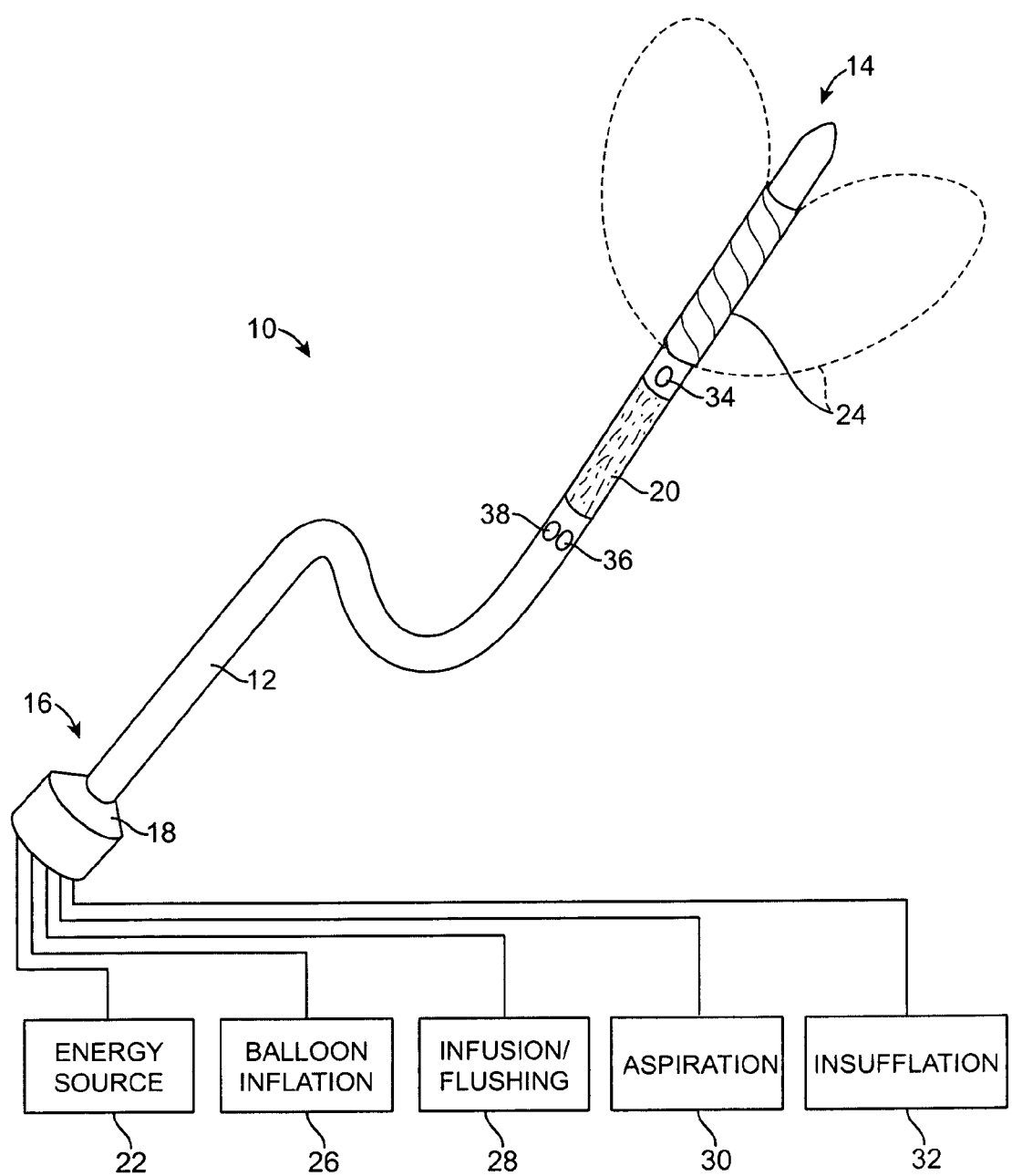
FIG. 1 is a schematic illustration of a device suitable for performing intraurethral prostatic tissue debulking in accordance with the principles of the present invention.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized $CO_2$ or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, and that the lumens and delivery means could be provided by additional catheters, tubes, and the like, for example including coaxial sleeves, sheathes, and the like which could be positioned over the shaft 12.

Figure 2A:
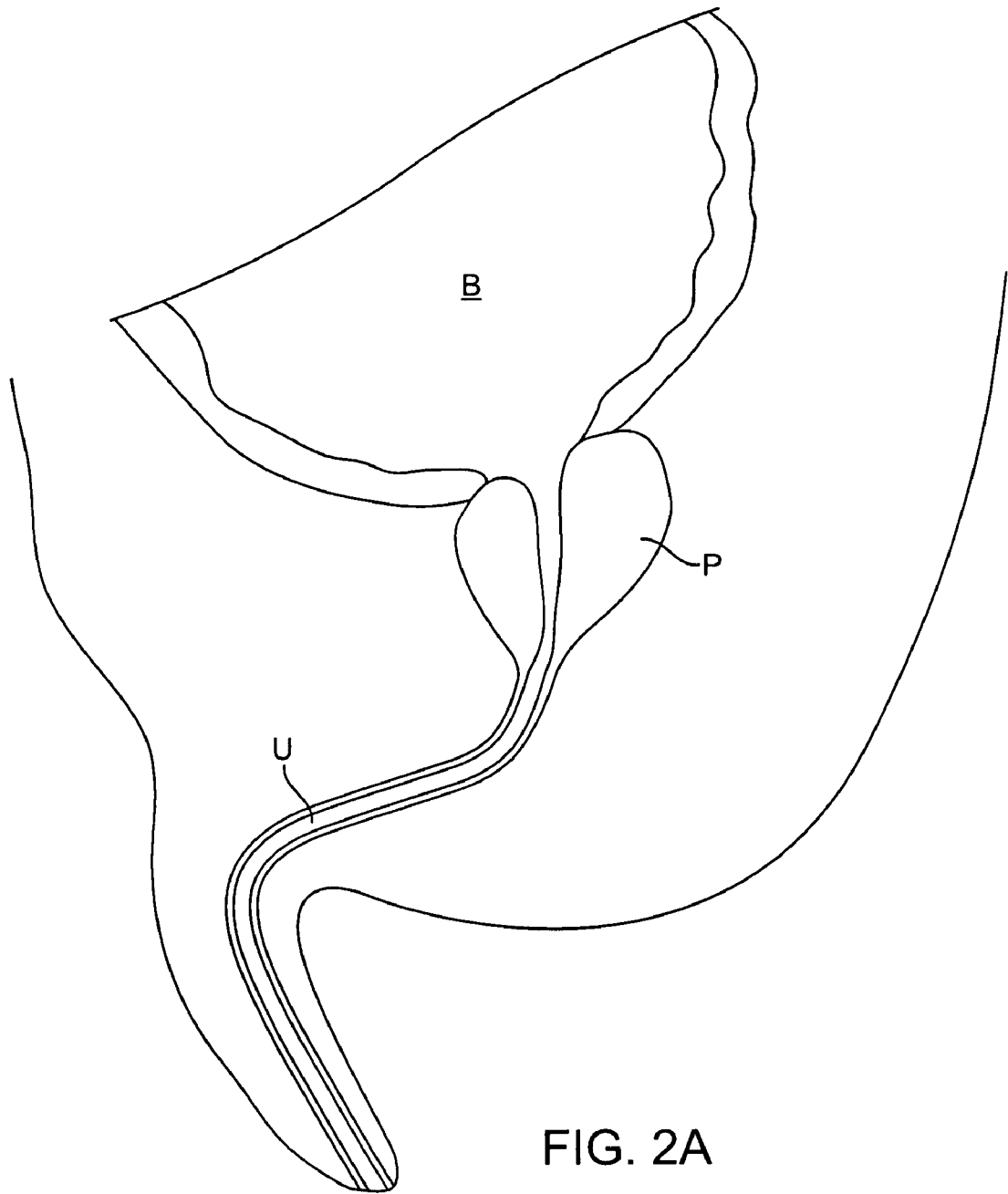
FIGS. 2A-2D illustrate use of the device of FIG. 1 in performing prostatic tissue debulking.
Figure 2B:
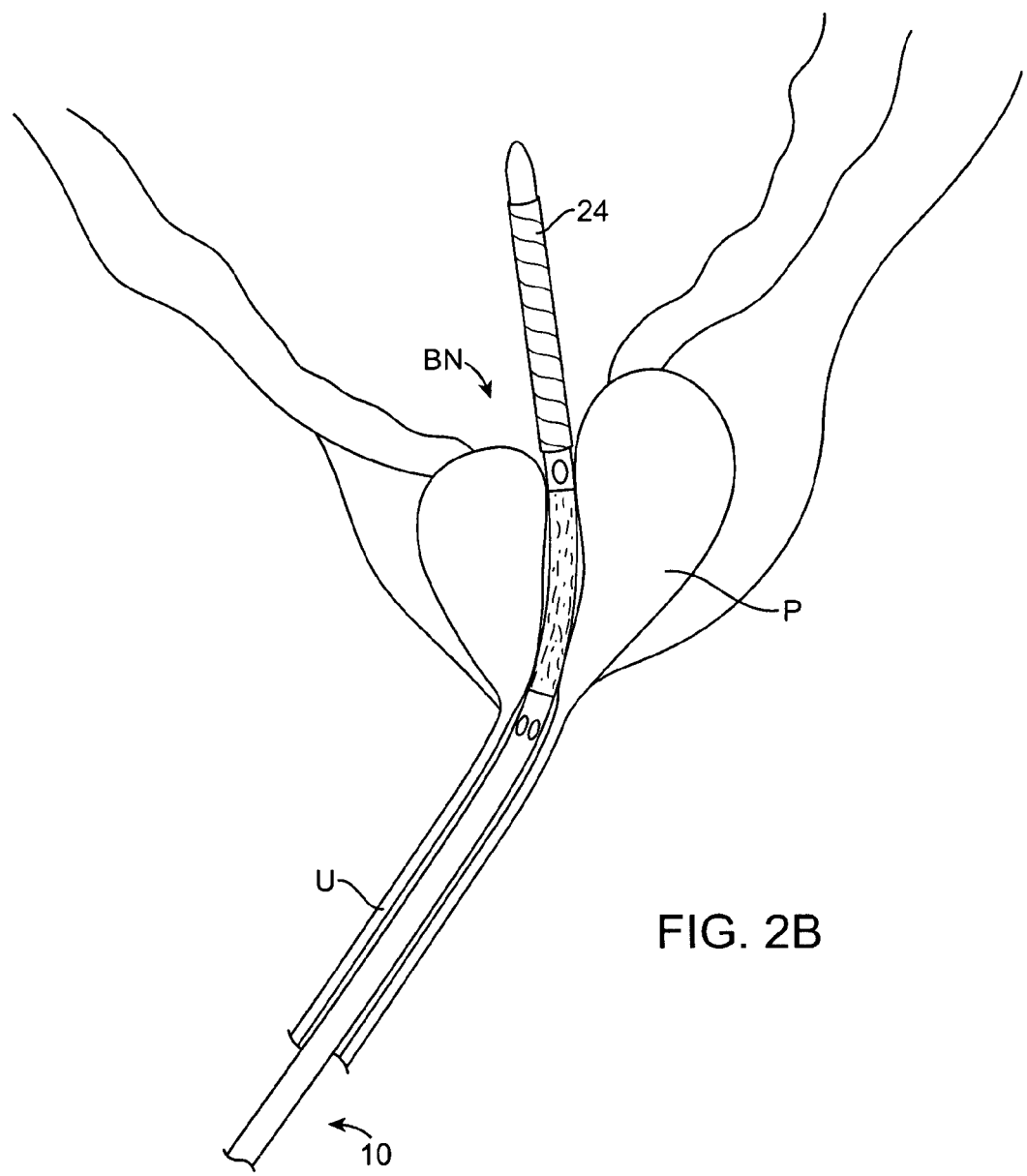
Figure 2C:
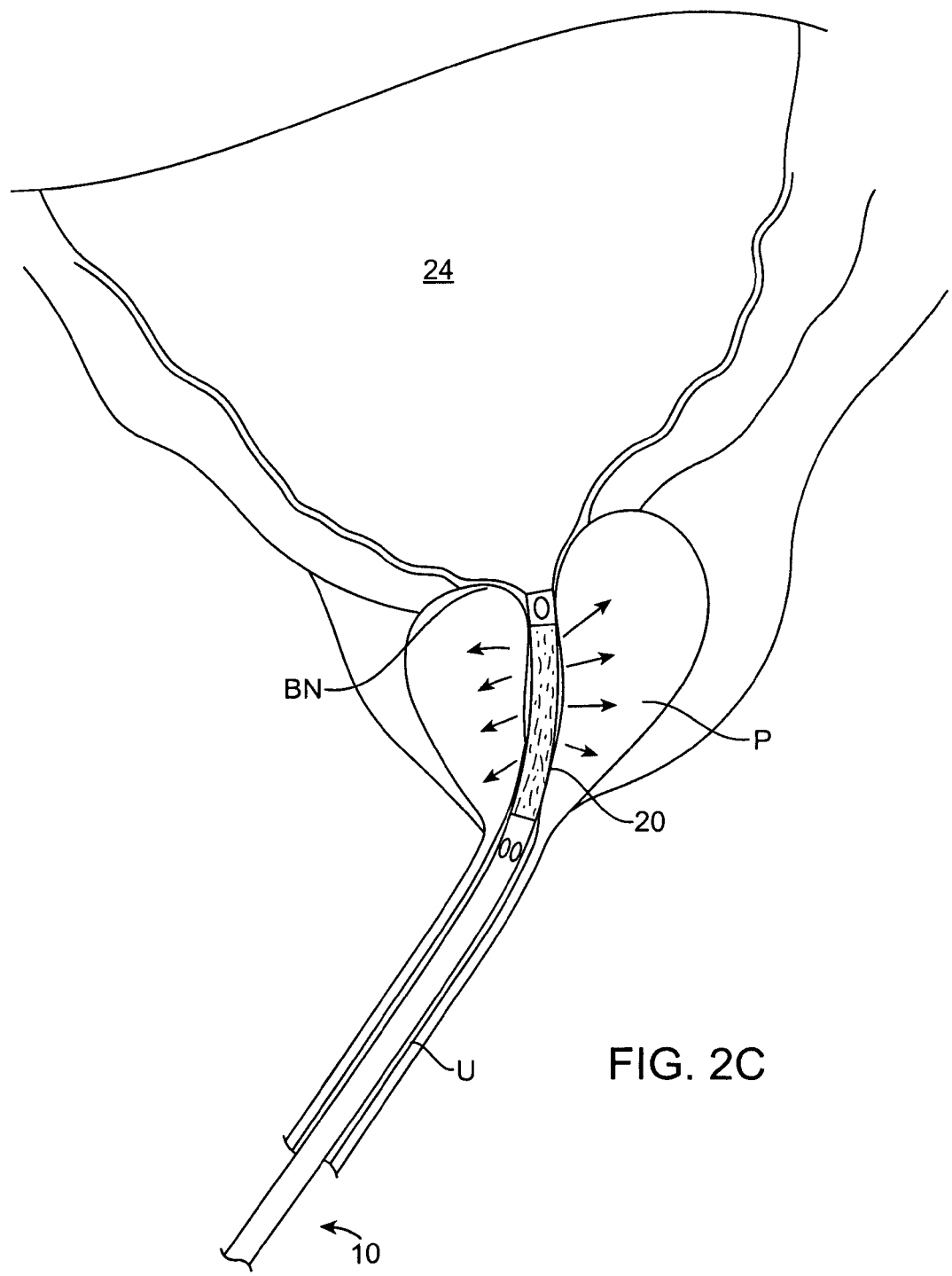
Figure 2D:
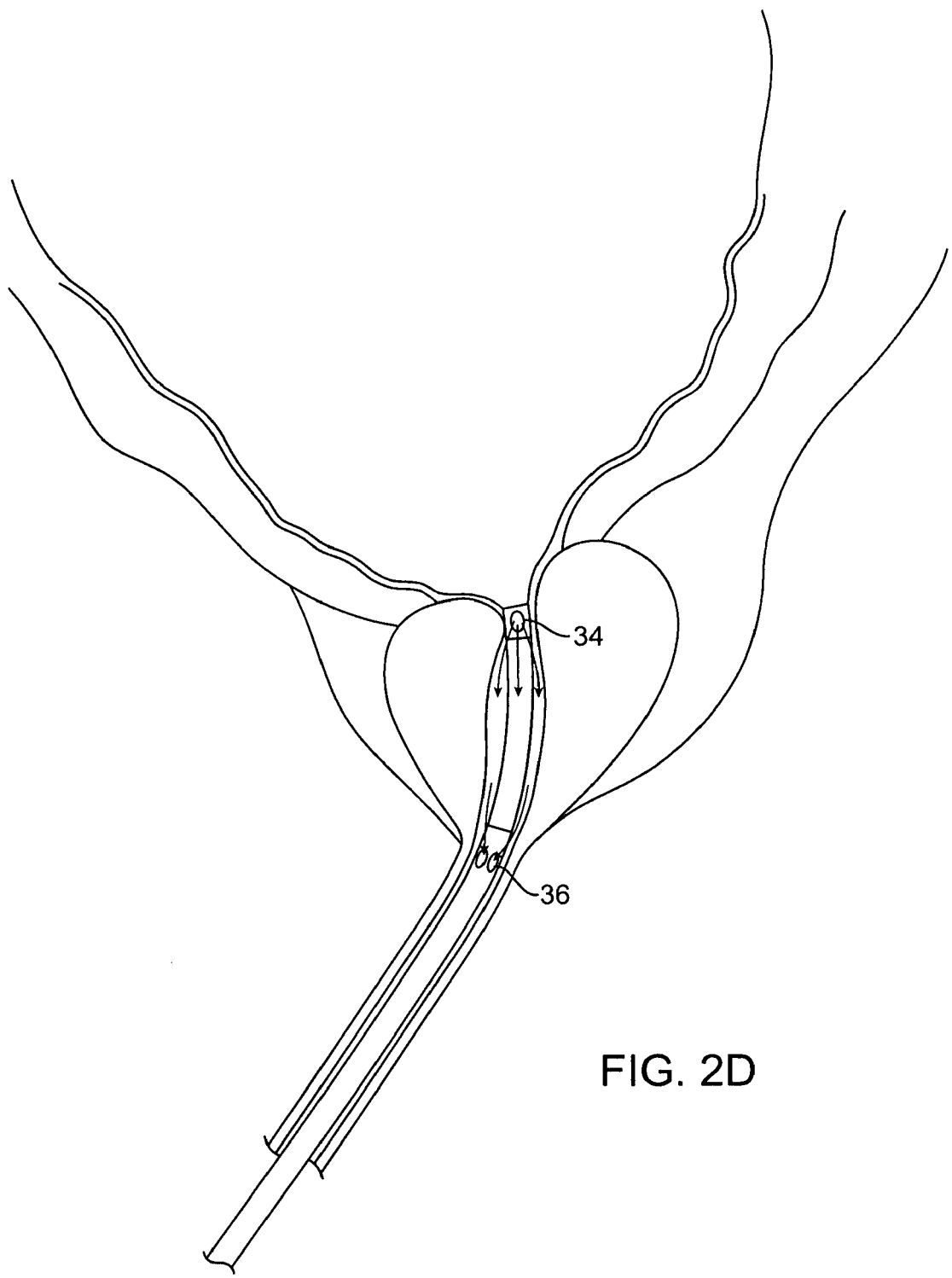

Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN and by spacing the distal end of the energy delivery region very close to the proximal end of the balloon, the delivery region can be properly located, typically having a length in the range from 0 mm to 5 mm, preferably from 1 mm to 3 mm. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a separate catheter device.

Figure 3:
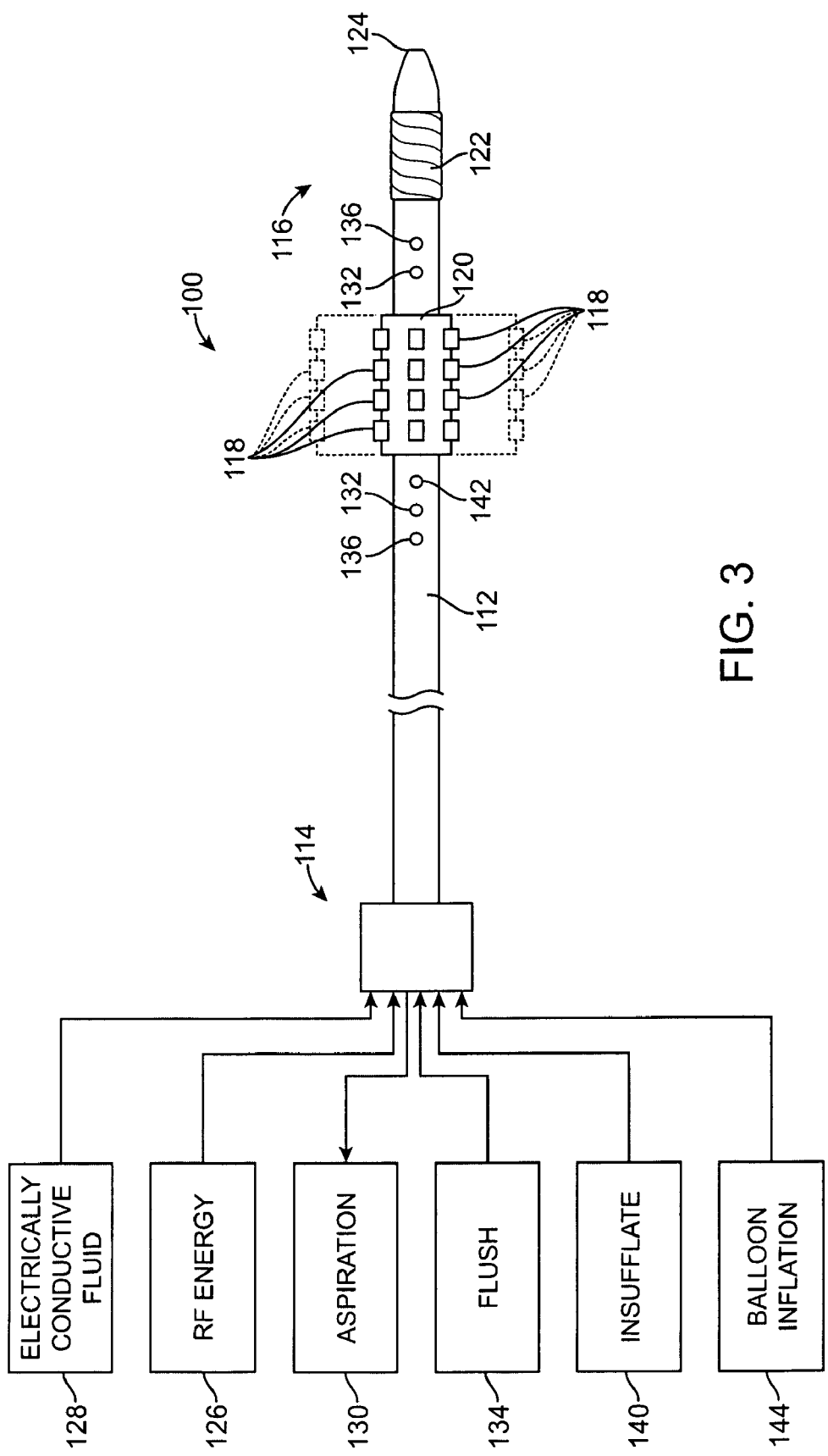
FIG. 3 illustrates a specific prostatic tissue treatment device incorporating the use of a radiofrequency saline plasma for performing prostatic tissue debulking.

Referring now to FIGS. 3-7, a number of representative energy delivery regions will be described. Referring now to FIG. 3, a first exemplary prostate resection device 110 constructed in accordance with the principles of the present invention comprises a shaft 112 having a proximal end 114 and a distal end 116. A plurality of nozzles 118 are mounted on the shaft 112 at a location spaced proximally from the distal end 116 by distance in the range from 1 cm to 5 cm. The nozzles, which are typically ceramic cores capable of generating a plasma or ports capable of directing a radially outward stream of electrically conductive fluid, may be mounted on structure 120, which allows the nozzles 118 to be moved radially outwardly, as shown in broken line in FIG. 3. An anchor 122, shown as an inflatable balloon is mounted on the distal end 116 of the shaft 112 at a location between the nozzles 118 and the distal tip 124. The expandable structure 122 will be capable of being expanded within the bladder to anchor the shaft 112 so that the nozzle array 118 lies within the prostate, as described in more detail below. The shaft 112 will include lumens, passages, electrically conductive wires, and the like, in order to deliver energy and materials from the proximal end 114 to the distal end 116 of the shaft. For example, an RF energy source 126 will be connected to the shaft 112, usually to the nozzles 118, in order to deliver RF energy to an electrically conductive fluid delivered from source 128 to the nozzles 118, typically through a lumen within the shaft 112. Other lumens, channels, or conduits will be provided in order to allow aspiration to a vacuum source 130 which is typically connected to one or more aspiration ports 132. Other conduits may be provided within the shaft 112 in order to permit introduction of a flushing fluid, such as saline, from a source 134 to ports 136. In other instances, it will be possible to connect the aspiration and flushing sources 130 and 134 to a common port so that aspiration and flushing may be conducted sequentially rather than simultaneously. Further optionally, internal lumens, conduits, or the like, may be provided in order to connect a source of insufflation 140 to one or more insufflation ports 142 on the shaft in the region of the array 118. Finally, internal lumens, conduits, or the like, may be provided for connecting balloon 122 to a balloon inflation source 144.

Figure 4:
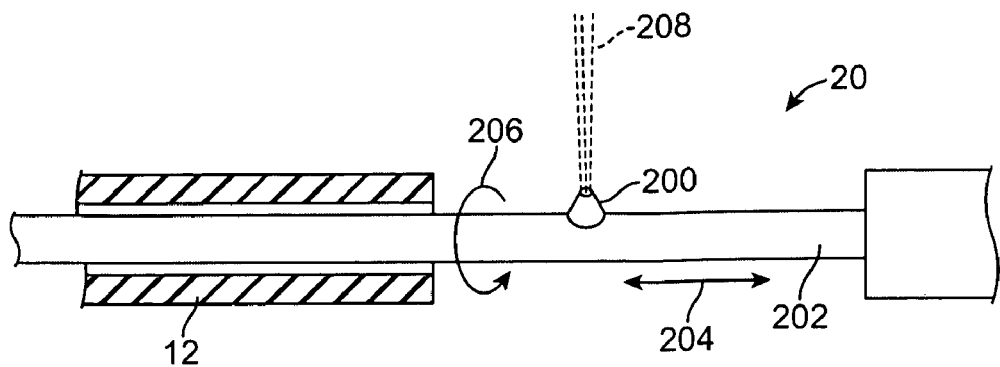
FIG. 4 illustrates an energy source suitable for use in the devices of the present invention, wherein the energy source delivers a high pressure fluid for tissue resection.

As shown in FIG. 4, an exemplary energy delivery region 20 can be formed by a high pressure nozzle 200 which is carried on a delivery tube 202 which is disposed within the shaft 12. Carrier tube 202 may be axially translated as shown by arrow 204 and/or rotated as shown by arrow 206 so that the high pressure stream 208 emanating from the nozzle 200 can be scanned or rastered over all or a selected portion of the urethra within the prostate. Specific pressures and other details for such high pressure water treatment are described, for example, in Jian and Jiajun, supra.

Figure 5:
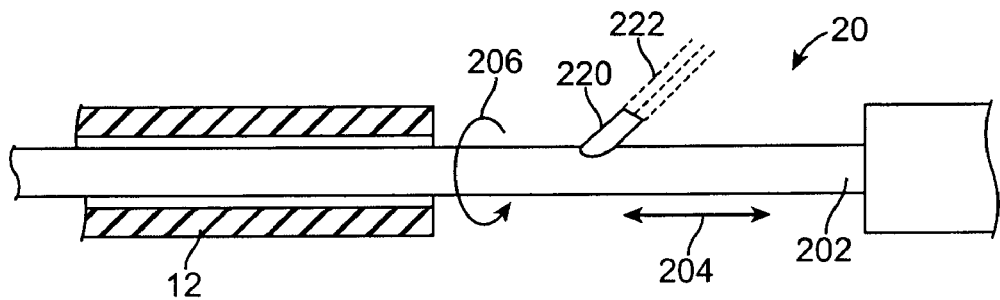
FIG. 5 illustrates an energy source suitable for use in devices of the present invention, wherein the energy source comprises a deflected optical waveguide for delivering laser energy to the prostatic tissue.

Referring now to FIG. 5, the energy source within the energy delivery region 20 may comprise a fiberoptic waveguide or fiber bundle 220 carried on the rotating and translating shaft 202. The optical waveguide 220 transmits laser or other coherent optical energy in a beam 222 which may be scanned or rastered over the urethral wall and prostatic tissue by rotating and/or translating the carrier tube 202.

Figure 6:
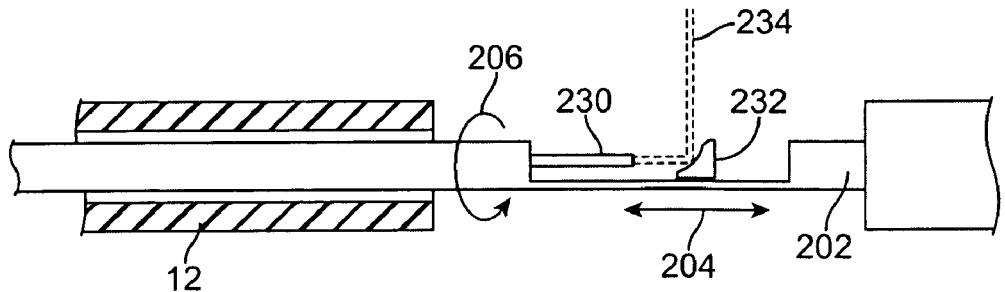
FIG. 6 illustrates a device similar to that shown in FIG. 5, except the optical waveguide directs laser energy at a mirror which laterally deflects the laser energy.

As shown in FIG. 6, laser energy from an optical waveguide or fiber bundle 230 may be directed axially against a mirror 232, where the waveguide and mirror are both carried on the rotating and axially translating carrier tube 202. Again, by rotating and/or translating the carrier tube 202, the emanating beam 234 can be scanned or rastered over the urethral wall.

Figure 7:
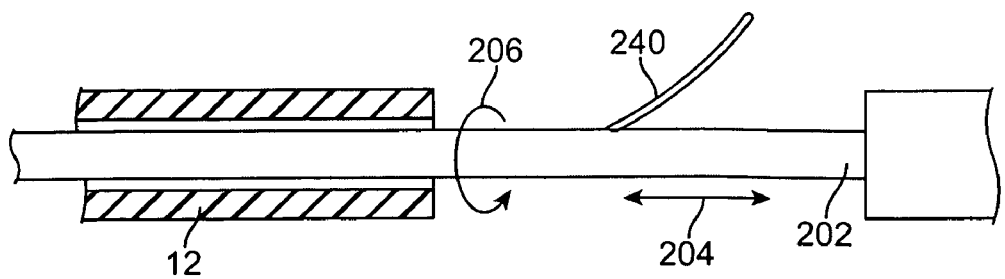
FIG. 7 illustrates an energy source suitable for use in the devices of the present invention, wherein the energy source comprises a laterally projecting electrode which can engage the urethral wall and prostatic tissue to deliver radiofrequency energy for tissue ablation.

Referring now to FIG. 7, in yet another embodiment, the rotating and axially translating tube 202 may carry an electrode 240 which projects laterally from the tube. The electrode 240 will be adapted for connection to a radiofrequency energy source so that, when the electrode contacts the urethral wall and prostatic tissue, radiofrequency energy can be delivered, either in a monopolar or bipolar mode. The radiofrequency energy can thus ablate the tissue over selected volumes and regions of the prostatic tissue. Optionally, by changing the nature of the radiofrequency energy, the electrode 240 could also be used to cauterize the tissue after it has been treated.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for prostate tissue resection, said method comprising:
    positioning a catheter assembly having a shaft which carries an energy source within a lumen of a urethra;
    directing a high pressure liquid stream radially outwardly from the energy source toward a wall of the urethra within the prostate; and
    moving the shaft within the catheter assembly to axially oscillate the energy source relative to the urethra, wherein the liquid stream mechanically resects a predefined volume of tissue surrounding the lumen, wherein the position of the catheter assembly remains positioned in the urethra while the energy source is axially oscillated relative to the shaft.

2. A method as in claim 1, wherein the liquid stream comprises an electrically conductive fluid, further comprising providing a radiofrequency current source and delivering radiofrequency current from said source to said liquid stream.

3. A method as in claim 1, further comprising introducing a pressurized gas to expand the urethra while the high pressure liquid stream is directed radially outwardly.

4. A method as in claim 1, further comprising aspirating the urethra to remove ablation products.

5. A method as in claim 4, further comprising flushing the urethra to help remove ablation products.

6. A method as in claim 5, wherein aspirating and flushing are performed with a device which also carries the energy source.

7. A method as in claim 1, wherein moving comprises a combination of rotation and axial translation.

8. A method as in claim 7, wherein rotation comprises rotational oscillation.

9. A method for debulking a prostate, said method comprising:
    axially oscillating and rotating a shaft within a catheter assembly disposed in a lumen of a urethra;
    stabilizing the catheter assembly in the urethra as the shaft is being axially oscillated; and
    directing a high pressure liquid stream radially outwardly from the shaft to mechanically resect tissue surrounding the urethra to debulk the prostate.

10. A method as in claim 9, wherein the high pressure liquid stream comprises a liquid and gas.

11. A method as in claim 9, wherein the shaft is axially oscillated to treat a predefined surface region of the urethra.

12. A method as in claim 11, wherein the predefined surface region is generally cylindrical.

* * * * *